United States Patent
Miller et al.

(10) Patent No.: US 12,134,084 B2
(45) Date of Patent: *Nov. 5, 2024

(54) CATALYST FOR DEHYDROGENATION OF LIGHT ALKANES

(71) Applicant: PURDUE RESEARCH FOUNDATION, West Lafayette, IN (US)

(72) Inventors: Jeffrey T. Miller, West Lafayette, IN (US); Zhenwei Wu, West Lafayette, IN (US); Evan C. Wegener, West Lafayette, IN (US); Stephen Purdy, West Lafayette, IN (US); Nicole J. Libretto, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 373 days.

This patent is subject to a terminal disclaimer.

(21) Appl. No.: 17/556,804

(22) Filed: Dec. 20, 2021

(65) Prior Publication Data

US 2022/0111359 A1    Apr. 14, 2022

Related U.S. Application Data

(63) Continuation of application No. 16/635,586, filed as application No. PCT/US2018/044587 on Jul. 31, 2018, now Pat. No. 11,203,010.

(60) Provisional application No. 62/545,972, filed on Aug. 15, 2017, provisional application No. 62/539,646, filed on Aug. 1, 2017.

(51) Int. Cl.
| | |
|---|---|
| *C07C 5/00* | (2006.01) |
| *B01J 21/06* | (2006.01) |
| *B01J 21/08* | (2006.01) |
| *B01J 23/00* | (2006.01) |
| *B01J 23/648* | (2006.01) |
| *B01J 23/652* | (2006.01) |
| *B01J 23/656* | (2006.01) |
| *B01J 37/00* | (2006.01) |
| *B01J 37/08* | (2006.01) |
| *B01J 37/16* | (2006.01) |
| *C07C 5/333* | (2006.01) |
| *B01J 21/02* | (2006.01) |

(52) U.S. Cl.
CPC ......... *B01J 23/6482* (2013.01); *B01J 21/063* (2013.01); *B01J 23/6522* (2013.01); *B01J 23/6562* (2013.01); *B01J 37/08* (2013.01); *B01J 37/16* (2013.01); *C07C 5/3337* (2013.01); *B01J 21/02* (2013.01); *B01J 21/08* (2013.01); *C07C 2523/42* (2013.01); *C07C 2523/44* (2013.01); *C07C 2523/46* (2013.01)

(58) Field of Classification Search
CPC ......... C07C 5/3337; B01J 23/00; B01J 37/08; B01J 21/083; B01J 23/6482; B01J 23/6522; B01J 23/6562

See application file for complete search history.

(56) References Cited

U.S. PATENT DOCUMENTS

| | | | |
|---|---|---|---|
| 3,748,260 | A | 7/1973 | Hayes |
| 4,595,673 | A | 6/1986 | Imai et al. |
| 5,660,714 | A | 8/1997 | Wittenbrink et al. |
| 6,177,585 | B1 | 1/2001 | Chen et al. |
| 8,309,782 | B2 | 11/2012 | Le Peltier et al. |
| 2003/0054955 | A1 | 3/2003 | Loewenstein |
| 2016/0059226 | A1 | 3/2016 | Tissler et al. |

OTHER PUBLICATIONS

International Search Report and Written Opinion for International Application No. PCT/US2018/044587 mailed on Oct. 10, 2018.
"Catalytic Dehydrogenation of Light Alkanes on Metals and Metal Oxides," Jesper J.H.B. Sattler, et al., Chemical Reviews 2014, vol. 114, pp. 10613-10653.

*Primary Examiner* — Sikarl A Witherspoon
(74) *Attorney, Agent, or Firm* — Edmonds & Cmaidalka, P.C.

(57) ABSTRACT

A novel catalyst composition and its use in the dehydrogenation of alkanes to olefins. The catalyst comprises a Group VIII noble metal and a metal selected from the group consisting of manganese, vanadium, chromium, titanium, and combinations thereof, on a support. The Group VIII noble metal can be platinum, palladium, osmium, rhodium, rubidium, iridium, and combinations thereof. The support can be silicon dioxide, titanium dioxide, aluminum oxide, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. The catalyst composition is an active and selective catalyst for the catalytic dehydrogenation of alkanes to olefins.

20 Claims, 8 Drawing Sheets

CATALYST FOR DEHYDROGENATION OF LIGHT ALKANES

CROSS REFERENCE TO RELATED APPLICATIONS

This application is a continuation of U.S. application Ser. No. 16/635,586, filed on Jan. 31, 2020, now issued as U.S. Pat. No. 11,203,010, which is a 371 application of PCT/US2018/044587 that was filed on Jul. 31, 2018, which claims benefit of U.S. Provisional Application No. 62/539,646 filed on Aug. 1, 2017, and benefit of U.S. Provisional Application No. 62/545,972 filed on Aug. 15, 2017, all of which are incorporated by reference herein.

BACKGROUND

The present disclosure is directed to new catalyst compositions for the dehydrogenation of light alkanes, especially gaseous alkanes, e.g., ethane, propane, butanes and/or pentanes, to their respective alkene derivatives. The alkenes, commonly known as olefins, have a high value as precursors to fuels, chemicals, and polymers such as polyethylene and polypropylene.

More efficient utilization of petroleum and gas reserves is an important strategy for the deployment of future energy generation. Shale gas has become an increasingly important source of natural gas in the United States, and the U.S. government's Energy Information Administration predicts that by 2040, approximately 70 percent of the United States' natural gas supply will come from shale gas. The transformation of shale gas to transportation fuels, fine chemicals and polymers is one of the strategies to utilize the shale gas reserves to their highest value.

Current state-of-the art olefin production includes thermal cracking of alkanes at high temperatures. For hydrocarbons with three or more carbons, thermal cracking results in mixtures of C—C and C—H cracked products, resulting in a mix of products that include propylene, ethylene, hydrogen, and methane. The resulting products must then be separated cryogenically at great cost.

Another known method for olefin production includes catalytic dehydrogenation (of propane) by metallic Pt or Cr oxide supported catalysts. Light alkane dehydrogenation is a reaction through which light alkanes are converted into light olefins and hydrogen. Thermodynamically, it is highly endothermic and equilibrium-limited. Due to equilibrium limitations, these selective alkane dehydrogenation reactions are typically carried out at a high temperature to maximize the olefin yield and minimize yields of undesired products such as alkynes, diolefins, and cracking products (lower molecular weight alkane olefin mixtures). A temperature typically above 500° C. is needed for the reaction to achieve theoretical conversion of 50% under a pressure of from 0.2 to 3 bar. At this temperature range, side reaction hydrogenolysis which results in methane and coke formation can occur and lead to fast catalyst deactivation if conventional noble metal catalysts are used. Selective conversion of $C_3$ or higher hydrocarbons is critical to advancing the art of alkane dehydrogenation. There is a need for improved catalyst compositions for the dehydrogenation reactions of alkanes to alkenes.

BRIEF DESCRIPTION OF THE DRAWINGS

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

DETAILED DESCRIPTION

Figure 1A:
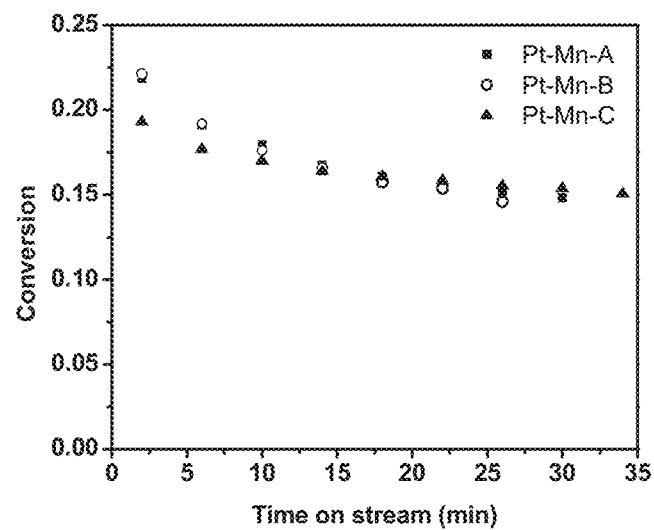
FIG. 1 is a graph of the conversion and selectivity of Pt—Mn catalysts A, B, and C in propane dehydrogenation.

The following detailed description illustrates embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken as limiting on the scope of the appended claims. In particular, an element associated with a particular embodiment should not be limited to association with that particular embodiment but should be assumed to be capable of association with any embodiment discussed herein.

Definitions

For the purpose of this description and appended claims, the following terms are defined.

The use of the terms "a" and "an" and "the" and similar referents in the context of describing the elements (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "alkane" or "paraffin" means substantially saturated compounds containing hydrogen and carbon only, e.g., those containing <1% (molar basis) of unsaturated carbon atoms. The term alkane encompasses $C_1$ to $C_6$ linear, iso, and cyclo alkanes.

As used herein, an "alkene" or "olefin" refers to any unsaturated hydrocarbon containing one or more pairs of carbon atoms linked by a double bond. The olefins described herein include cyclic or aliphatic olefins, and include mono-olefins, di-olefins, tri-olefins, etc.

As used herein, a "bimetallic catalyst" is a catalyst having at least two metal components. The term does not limit the number of metal components to only two. The two metals are, at least partially present in the metallic phase and/or in a metallic alloy state.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means hydrocarbon having at least n carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule.

As used herein, a "catalyst" is any substance or material which changes the rate of conversion of alkanes to alkenes but is not, itself, consumed.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The present disclosure relates generally to dehydrogenation reactions of alkanes to olefins.

More particularly, the present disclosure relates to catalysts which can enable dehydrogenation reactions of alkanes to olefins. Embodiments of the present disclosure provide a method to produce such catalysts. The catalytic dehydrogenation of hydrocarbons according to the formula $C_nH_{2n+2} \leftrightarrow C_nH_{2n}+H_2$, is a highly endothermic equilibrium reaction, the reaction rate of which is limited thermodynamically and which depends on the respective partial pressures and temperature. The dehydrogenation reaction is favored by low partial pressures of the hydrocarbons and by high temperatures.

The present disclosure is directed to novel catalyst compositions and their respective use in the dehydrogenation of alkanes to olefins. The catalyst is bimetallic and comprises a combination of a Group VIII noble metal, such as platinum or palladium, and a metal selected from the group consisting of manganese, vanadium, chromium and titanium, on a support. Non-limiting examples of support can include silicon dioxide, aluminum oxide and titanium dioxide. The catalyst is an active and selective catalyst for the catalytic dehydrogenation of alkanes to olefins while retaining high activity and selectivity even following repeated regeneration by burning coke in oxygen.

Commercially available light alkane dehydrogenation catalysts currently in use are Pt—Sn and CrOx based catalysts supported on an alkali (Na/K) modified alumina. A Pt—Sn catalyst is used in the Oleflex process which utilizes a continuous fluidized catalyst bed. The Oleflex process is commercially offered by Honeywell UOP. Alternately a CrOx catalyst is used in the Catofin process licensed by Lummus Technology, a CB&I company, which uses parallel fixed beds. Both of these catalysts are reported to achieve selectivity above 90%. Nevertheless, frequent regeneration is needed in industrial operation and the catalysts have a total life of approximately 1 to 3 years.

Due to equilibrium limitations, these selective alkane dehydrogenation reactions are typically carried out at a high, but narrow temperature range to maximize the alkene yield and minimize yields of undesired products such as alkynes, diolefins, and cracking products (lower molecular weight alkane olefin mixtures). Useful catalysts must exhibit high activity and selectivity for the desired dehydrogenation process and a minimal rate of deactivation. Dehydrogenation reactions are known to produce coke which is highly refractory and the coke formation leads to catalyst deactivation. Coke removal can require combustion in oxygen containing gas at temperatures greater than 600° C. Desirable catalysts, therefore, must retain high alkane dehydrogenation activity following high temperature regeneration.

The catalysts of the present disclosure can be prepared by impregnating a support material with manganese, vanadium, chromium, titanium, or combinations thereof, to form a precursor. The precursor can then be dried and calcined. The amount of manganese, vanadium, chromium, titanium, and/or combinations thereof, to be impregnated can range from about 0.001 wt % to about 40 wt %, optionally about 0.01 wt % to about 20 wt %, optionally from about 0.3 wt % to about 10 wt % calculated on an elemental basis of the final catalyst composition.

A metal selected from the group consisting of Group VIII noble metal(s) is then impregnated onto the modified support material to provide dehydrogenation functions. The Group VIII noble metal can be selected from the group of platinum, palladium, osmium, ruthenium, iridium, rhodium, or combinations thereof. In an embodiment either platinum, palladium, or combinations thereof are employed. The amount of noble metal loading to be impregnated can range from about about 0.001 wt % to about 40 wt %, optionally about 0.01 wt % to about 10 wt % calculated on an elemental basis of the final catalyst composition. It is desirable that the catalyst will contain from about 0.1 wt % to about 5 wt % noble metal, most desirable about 0.3 wt % to about 2 wt % noble metal. As an example, platinum loading on silica can be accomplished via incipient wetness impregnation techniques using an aqueous solution of platinum tetraammine nitrate $Pt(NH_3)_4(NO_3)_2$ having a pH adjusted with ammonium hydroxide to a value greater than about 10. Following noble metal loading the catalyst can be dried, calcined and reduced. Platinum loading on alumina can be accomplished via incipient wetness impregnation techniques using an aqueous solution of chloroplatinic acid $H_2PtCl_6$ having a pH adjusted solution with HCl to a value less than about 2.

The impregnations can be accomplished via the incipient wetness technique; however, other suitable techniques known to those skilled in the art are also suitable. An absorption technique from a dilute or concentrated solution, with subsequent filtration or evaporation to effect uptake of the metallic component, may also be used. Frequently, the pH of the solution will be adjusted to provide for optimum intercalation. In embodiments, for catalysts prepared on a silica support the pH is adjusted to range between 8-14, optionally from 9-13, optionally from 10-12, optionally from 10.5-11.5 for catalyst prepared on silica supports. For catalysts prepared on alumina supports, the pH of the solution can range from 1-7, optionally from 1.5-5 and preferably from about 2-4. Contacting time can be anywhere from at least about 1 minute to about 24 hours, optionally about 1 minute to 8 hours, optionally, about 1 minute to about 1 hour. In some instances, the higher the contacting temperature the shorter the contacting time that is necessary. Such contacting times can be readily determinable by one skilled in the art. The resulting material can then be separated by any conventional means, washed and dried. The impregnated support can then be dried followed by calcination and reduction.

The drying can be conducted at ambient temperature at first, such as for about 3 hours, followed by an elevated temperature, such as about 125° C. for about 8 hours. The calcination can be conducted at increasingly elevated temperature, such as at a temperature from 200° C. to 650° C., in the presence of oxygen, or in an air stream, or in the presence of a mixture of oxygen and an inert gas. In an example, the calcination can be about 200° C. for 30 minutes, and then 550° C. for 30 minutes or longer. The calcination process can be a staged calcination, wherein the temperatures are changed throughout the process. The temperature changes need not be a linear increase, but can be increased for example from 200° C. to 400° C. and held at 400° C. followed by another increase, etc. However, linear increases in temperature can also be used. This calcination can be conducted for periods ranging from about 30 minutes to 24 hours in either flowing or static gases. After calcination, the catalyst can be reduced in flowing hydrogen, or a hydrogen containing inert gas stream, at increasingly elevated temperatures, such as at 200° C. for 30 minutes and then at 550° C. for 30 minutes. The times, temperatures and rates of change during the drying, calcination and reducing process of the impregnated support are variable, can be readily determinable by one skilled in the art, and is not to be a limitation upon the present disclosure.

The metals can be added in any suitable manner known in the art, such as non-limiting examples of supported on a substrate or an inert support, added to a binder, placed on or within a zeolite or other catalyst support, such as by ion exchange, incipient wetness impregnation, pore volume impregnation, soaking, percolation, wash coat, precipitation, and gel formation.

The various elements that make up the components for the catalyst can be derived from any suitable source, such as in their elemental form, or in compounds or coordination complexes of an organic or inorganic nature, such as carbonates, oxides, hydroxides, nitrates, acetates, chlorides. The elements and/or compounds can be prepared by any suitable method known in the art for the preparation of such materials.

The term "support" or "substrate" as used herein is not meant to indicate that this component is necessarily inactive, while the other metals and/or promoters are the active species. On the contrary, the substrate can be an active part of the catalyst. The term substrate or support would merely imply that the substrate makes up a significant quantity, generally 10% or more by weight, of the entire catalyst. The active metals individually can range from 0.001% to 40% by weight of the catalyst, optionally from 0.3% to 10%. If more than one active metal is combined, they together generally can range from 0.001% up to 40% by weight of the catalyst. The manganese, vanadium, chromium, titanium, and combinations thereof can, at least partially be present in the metallic phase. The manganese, vanadium, chromium, titanium, and combinations thereof can, at least partially be present in an alloy state.

The supports of the present disclosure can be any suitable support, such as for non-limiting examples: silicon dioxide, aluminum oxide, titanium dioxide, zeolites, silica-alumina, cerium dioxide, zirconium dioxide, magnesium oxide, silica pillared clays, metal modified silica, metal oxide modified silica, silica-pillared clays, metal oxide modified silica-pillared clays, silica-pillared micas, metal oxide modified silica-pillared micas, silica-pillared tetrasilicic mica, silica-pillared taeniolite, and combinations thereof. Such supports are commercially obtainable or prepared by techniques known to those skilled in the art.

Prior art also describes the use of metal-containing zeolite catalysts, in which the metal is incorporated into the zeolite structure by some process, such as ion exchange or impregnation. However, swings in catalytic activity may occur in the case of a metal impregnated catalyst as metal can be lost from the pore structure of a zeolite or molecular sieve type substrate. Another drawback is the high probability of plugging of pores with coke when the metal is incorporated into a zeolite or molecular sieve type structure.

In one embodiment, the catalyst can be prepared by combining a substrate with the active metal elements. Embodiments of a substrate can be a molecular sieve, from either natural or synthetic sources. Zeolites can be an effective substrate, can be commercially available, and are well known in the art. Alternate molecular sieves also contemplated are zeolite-like materials such as for example crystalline silicoaluminophosphates (SAPO) and the aluminophosphates (ALPO).

The present disclosure is not limited by the method of catalyst preparation, and all suitable methods should be considered to fall within the scope herein. Conventional methods include co-precipitation from an aqueous, an organic, or a combination solution-dispersion, impregnation, dry mixing, wet mixing or the like, alone or in various combinations. In general, any method can be used which provides compositions of matter containing the prescribed components in effective amounts. According to an embodiment the substrate is charged with active metal via an incipient wetness impregnation. Other impregnation techniques such as by soaking, pore volume impregnation, or percolation can optionally be used. Alternate methods such as ion exchange, wash coat, precipitation, and gel formation can also be used.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition can be calcined in the presence of a free oxygen-containing gas, usually at temperatures between about 200° C. and about 600° C. for from 1 to 24 hours. The calcination can be in an oxygen-containing atmosphere, or alternately in a reducing or inert atmosphere.

Binder material, extrusion aids or other additives can be added to the catalyst composition or the final catalyst composition can be added to a structured material that provides a support structure. For example, the catalyst component and/or the composite catalyst can include an alumina or aluminate framework as a support. Upon calcination these elements can be altered, such as through oxidation which would increase the relative content of oxygen within the final catalyst structure. The combination of the composite catalyst of the present invention combined with additional elements such as a binder, extrusion aid, structured material, or other additives, and their respective calcination products, are included within the scope of the invention.

The prepared catalyst can be ground, pressed, sieved, shaped and/or otherwise processed into a form suitable for loading into a reactor. The reactor can be any type known in the art, such as a fixed bed, fluidized bed, or swing bed reactor. Optionally an inert material, such as quartz chips, can be used to support the catalyst bed and to locate the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 15 min to 3 hours. Then, the reactor can be brought to the operating temperature of the reactor, for example 150° C. to 900° C., or optionally down to atmospheric or other desired temperature. The reactor can be kept under an inert purge, such as under a nitrogen or helium purge.

The catalyst of the present disclosure can be contacted with a feedstream containing $C_2$ to $C_5+$ alkanes under dehydrogenation conditions, for a time and at a temperature sufficient to produce olefins. It is desirable that mono-olefins will be produced. The alkanes may be co-fed with a stream of $H_2$ and/or inert gas. The $H_2$:alkane or inert:alkane ratio can range from about 0 to 5, optionally 0 to 2.0. Steam may also be co-fed if desired as a diluent or as a heat transfer agent.

In an embodiment the catalyst of the present disclosure can undergo in-situ regeneration, which can lower operating costs by decreasing the amount of time the reactor must be offline. The regeneration can be done at the reaction temperature by burning of carbon with oxygen concentrations between 0.1 and 20%, optionally from 0.3-10%, and optionally from 0.5 to 3%. Alternatively, the catalyst can be regenerated with hydrogen at the reaction temperature. In an embodiment the catalyst of the present disclosure can undergo ex-situ regeneration.

In another embodiment, the disclosure is a process for the dehydrogenation of alkanes to olefins. The process includes the steps of introducing an alkane feedstock into a reaction chamber, passing the feedstock over a dehydrogenation catalyst at reaction conditions effective to provide a product containing olefin hydrocarbons, and regenerating the catalyst in-situ, when necessary.

The alkane feedstock can be alkanes containing less than 10 carbon atoms. The feedstock can consist primarily of $C_2$-$C_6$ alkanes. An embodiment of the invention provides for the use of ethane or propane or butane or a mixture of these gases as the starting material. Embodiments of the invention are particularly suitable for the production of ethene or propene or butenes or a mixture of these olefins. The alkane feedstock can be obtained from the side product of various hydrocarbon processing plants, for instance, the offgas of an FCC cracker or other refinery processes, refinery fuel gas, or shale gas hydrocarbons. One source of alkane feedstock is from natural gas liquids (NGL's) that can be extracted by gas processing plants, often a cryogenic process that extract the NGL's from a gas stream, such as a gas stream produced from a shale formation. One source of alkane feedstock is liquid petroleum gas (LPG), which consists mainly of the propane and butane fraction and can be recovered from gas and oil fields and petroleum refining operations. Co-feed can contain hydrogen. Since the catalyst can withstand steam at the temperatures used for this process, steam can be used as a co-feed to increase conversion while reducing coke formation. In an illustrative embodiment the alkane feed can contain primarily ethane. In an illustrative embodiment the alkane feed can contain primarily propane. In an illustrative embodiment the alkane feed can contain primarily butane. In an illustrative embodiment the alkane feed can contain primarily ethane and propane. In an illustrative embodiment the alkane feed can contain primarily propane and butane. In an illustrative embodiment the alkane feed can contain primarily butane and pentane. In an illustrative embodiment the alkane feed can contain primarily $C_3$-$C_6$ alkanes. In an illustrative embodiment the alkane feed can contain primarily $C_2$-$C_6$ alkanes.

The reaction chamber used in the dehydrogenation reaction can house any suitable catalyst system, such as a fixed catalyst bed, a moving bed or a fluidized bed. Single or multiple catalyst beds can be used, and the reactor can be a swing reactor. The catalysts described herein may be used in any suitable reactor. The process could utilize a series of fixed bed reactors, where each reactor could be independently regenerated, a moving bed reactor where the catalysts moves through the reactor and is regenerated in a separate section of the plant, or a fluidized bed reactor, where the catalyst is circulated through the reactor and regenerated in a separate vessel.

The reaction can take place at a temperature of from 350° C. to 1000° C., optionally from 400° C. to 800° C., optionally from 450° C. to 750° C. For example, the reaction may take place at up to 400° C., 450° C., 500° C., 550° C., 600° C., 650° C., 700° C., 750° C., 800° C., 850° C., 900° C., 950° C., or 1000° C. The pressure can be in the range of from 3 psig to 600 psig, optionally from 3 psig to 300 psig, optionally from 3 psig to 150 psig. The weight hourly space velocity can be from 0.3 to 20 hr$^{-1}$, optionally from 0.3 to 10 hr$^{-1}$, and optionally from 0.3 to 3 hr$^{-1}$.

The dehydrogenation reaction can be performed adiabatically or non-adiabatically or approximately isothermally. If the dehydrogenation is performed in an adiabatically operated catalyst bed, the endothermic reaction will cause the temperature to decrease over the length of the catalyst bed. The reaction rate in the catalyst bed is thus limited so that several catalyst beds are typically required to achieve the desired high reaction rates and re-heating is necessary downstream of each catalyst bed. In order to achieve reasonable reaction rates, several catalyst beds are normally arranged in series and the reaction system is re-heated downstream of each catalyst bed.

If the dehydrogenation is performed in a non-adiabatically operated catalyst bed, the catalyst bed can be heated in order to maintain a high temperature. Because of the fact that the temperature in the reaction system is kept constant, the reaction rates may be kept appropriately high. Because of the location of the point of thermodynamic equilibrium, however, the disadvantage is that these high reaction rates can only be achieved at high temperatures, as a result of which the selectivity of olefin formation may be reduced. Hence, consecutive reactions will increasingly take place, so that undesired products may form, such as $CH_4$, $C_2H_4$, $C_2H_6$ and coke.

The by-products thus formed, especially finely dispersed coke, can precipitate in the course of the reaction on the catalyst, thus causing its state to change continually. The catalyst becomes coated with an undesired substance and is thus less accessible for the reactants. This means that the catalyst becomes deactivated. The activity of the catalyst for alkane dehydrogenation and the selectivity for alkene formation may in turn deteriorate. This would result in deterioration of the efficiency of the process as a whole. Because of operational requirements, such a deactivation can only be tolerated up to certain limit, because an economically viable operation of the plant could no longer be guaranteed. In order to counter-act this negative influence on the process, the catalyst will have to be regenerated after a certain reaction period in order to recover its activity.

Depending on its characteristics, the catalyst can be regenerated by bringing it in contact with an oxygen-bearing gas under conditions defined for the regeneration of the catalyst. The conditions for such a regeneration may differ from those required for the dehydrogenation. An oxygen-bearing gas diluted with steam may also be fed through the catalyst. As a result of this procedure, the by-products on the catalyst are reduced, with the result that the catalyst can regain its activity. If an oxygen-bearing gas diluted with steam is used for catalyst regeneration, the carbon-bearing deposit reacts to form carbon dioxide as the main product. The carbon-bearing deposit is converted to gaseous products by this reaction and is removed from the system.

As the conditions for the alkane dehydrogenation process differ from the catalyst regeneration process, the alkane dehydrogenation process will be interrupted after a certain period of operation and substituted by the catalyst regeneration process. Thereafter, the reactor bed is purged and again made available for dehydrogenation. Both these processes, i.e. the alkane dehydrogenation and catalyst regeneration, are thus performed periodically. In order to render the overall process economically efficient, this can take place in two or a plurality of catalyst beds, in which the reaction and regeneration processes are alternately implemented. In order to ensure optimum catalyst regeneration, regeneration process should be instrumented and monitored.

The reaction products can be processed and separated by cooling or other standard recovery or separation techniques.

The following examples are given to provide a better understanding of the present invention and are not intended to limit the scope of the invention in any way.

Experimental Data

Comparative Monometallic Pt Catalyst

A monometallic Pt catalyst, Pt-A, (2 wt % Pt supported on Davisil 636 silica gel from Sigma-Aldrich, 480 $m^2/g$ and 0.75 mL/g pore volume) was synthesized using the incipient wetness impregnation (IWI) method. An amount of 0.20 g of tetraammineplatinum nitrate $Pt(NH_3)_4(NO_3)_2$ (Sigma-Aldrich) was dissolved in 3 mL of distilled $H_2O$. A 30% ammonium hydroxide solution (Sigma-Aldrich) was then added to the solution until the pH reached 11. The obtained Pt precursor solution was added dropwise to 5 g of silica and stirred. After drying at 125° C. overnight (for approximately 16 hours), the sample was calcined at 225° C. for 3 hours and reduced at 550° C. in 5% $H_2/N_2$ at 100 $cm^3/min$ flowrate for 30 minutes. Catalyst Pt had a platinum loading of 2.0 wt %.

Bimetallic Pt—Mn Catalysts

Bimetallic Pt—Mn (A-D) catalysts were synthesized by sequential incipient wetness impregnation (s-IWI) under controlled pH conditions. For Pt—Mn-A catalyst, 0.68 g of manganese nitrate tetrahydrate $Mn(NO_3)_2.4H_2O$ (Sigma-Aldrich) together with 1.05 g Citric acid (Sigma-Aldrich) were dissolved in 3 mL of $H_2O$. A 30% ammonium hydroxide solution was then added to this solution to obtain a pH of 11. Additional water was added to this solution so that the total volume is 7.5 mL. This mixture was then added dropwise to 10 g of silica and stirred. The obtained $Mn/SiO_2$ catalyst precursor was dried overnight (for approximately 16 hours) at 125° C. and then calcined at 550° C. for 3 hours. A second IWI was conducted to load the Pt on the $Mn/SiO_2$. 0.20 g of tetraammineplatinum nitrate $Pt(NH_3)_4(NO_3)_2$ (Sigma-Aldrich) were dissolved in 3 mL of $H_2O$. A 30% ammonium hydroxide solution (Sigma-Aldrich) was added to the solution until the pH reached 11 before they were added dropwise to 5 g of the obtained $Mn/SiO_2$. This catalyst was dried overnight (for approximately 16 hours) at 125° C., calcined at 225° C. for 3 hours and then reduced at 550° C. in 5% $H_2/N_2$ at 100 $cm^3/min$ for 0.5 hours. Catalyst Pt—Mn-A had a platinum loading of 2 wt % and a manganese loading of 2.0 wt %.

The same process is used for preparation of Pt—Mn-B, C and D catalyst, except that 1.14 g of Manganese nitrate tetrahydrate $Mn(NO_3)_2.4H_2O$ together with 1.75 g Citric acid were dissolved in the first step for Pt—Mn-B; 1.36 g of Manganese nitrate tetrahydrate $Mn(NO_3)_2.4H_2O$ together with 2.10 g Citric acid were dissolved in the first step for Pt—Mn-C, and 2.28 g of Manganese nitrate tetrahydrate $Mn(NO_3)_2.4H_2O$ together with 3.50 g Citric acid were dissolved in the first step for Pt—Mn-D. Catalyst Pt—Mn—B had a platinum loading of 2 wt % and a manganese loading of 2.5 wt %. Catalyst Pt—Mn-C had a platinum loading of 2 wt % and a manganese loading of 3.0 wt %. Catalyst Pt—Mn-D had a platinum loading of 2 wt % and a manganese loading of 5.0 wt %.

Bimetallic Pt—V Catalysts

Bimetallic Pt—V catalysts (E-F) were prepared by sequential incipient wetness impregnation on Davasil 636 (Sigma-Aldrich). The vanadium precursor was prepared by heating an aqueous 2:1 molar solution of $NH_4VO_3$ ammonium metavanadate (Sigma-Aldrich) and oxalic acid dihydrate (Sigma-Aldrich) to 100° C. for 1 hour. The prepared solution was impregnated to the pore volume of the support and dried at room temperature for 3 hours, and overnight (for approximately 16 hours) at 125° C. The dried catalyst was then calcined at 400° C. for 3 hours. Platinum loading was accomplished using an aqueous solution of platinum tetraammine nitrate $Pt(NH_3)_4(NO_3)_2$ (Strem). The pH of the Platinum tetraammine nitrate solution was adjusted to 10 with ammonium hydroxide (Sigma-Aldrich). The fresh Pt—V catalyst was then dried at room temperature for 3 hours and then overnight (for approximately 16 hours) at 125° C. The dried catalyst was then calcined for 3 hours at 250° C. After calcination the catalyst was reduced in flowing hydrogen at 200° C. for 30 minutes, and then 550° C. for 30 minutes. Catalyst Pt—V-E had total platinum loading of 5 wt %, and vanadium loading of 5 wt %. Catalyst Pt—V-F had platinum loading of 5 wt % and vanadium loading of 2.5 wt %.

Bimetallic Pt—Cr Catalysts

Bimetallic Pt—Cr (G-L) catalysts were synthesized by sequential incipient wetness impregnation (IWI) on Davasil 636 using controlled pH conditions. A solution based on the desired chromium loading was made using chromium nitrate nonahydrate $Cr(NO_3)_3.9H_2O$ (Sigma-Aldrich) and citric acid (Sigma Aldrich) in a 1:1 molar ratio, both dissolved in 2 mL of water. A 30% ammonium hydroxide solution was then added to this solution to obtain a pH of 11. Additional water was added to the solution so that the total volume was 5 mL. This mixture was then added dropwise to 5 g of $SiO_2$ and stirred. The resulting $Cr/SiO_2$ catalyst was dried overnight (for approximately 16 hours) at 125° C. and then calcined at 350° C. for 3 hours. A second IWI was performed to load Pt on the $Cr/SiO_2$. A solution was made by dissolving platinum tetraammine nitrate $Pt(NH_3)_4(NO_3)_2$ (Strem) in 2 mL of water. The pH was adjusted to 11 using 30% ammonium hydroxide solution and additional water was added so that the total volume was 5 mL. The mixture was added dropwise to 5 g of $Cr/SiO_2$. The resulting $Pt—Cr/SiO_2$ catalyst was dried overnight (for approximately 16 hours) at 125° C. and then calcined at 250° C. for 3 hours. The catalyst was reduced in flowing hydrogen at 200° C., 250° C., and then 550° C., each held for 30 minutes. Catalyst Pt—Cr-L was synthesized in the same manner described above, but alumina was used as the support. Catalyst Pt—Cr-G contained platinum loading of 2 wt % and chromium loading of 0.5 wt % Cr. Catalyst Pt—Cr-H contained platinum loading of 2 wt % and chromium loading of 1 wt %. Catalyst Pt—Cr-I contained platinum loading of 2 wt % and chromium loading of 3 wt %. Catalyst Pt—Cr-J contained platinum loading of 2 wt % and chromium loading of 5 wt %. Catalyst Pt—Cr-K contained platinum loading of 2 wt % and chromium loading of 7 wt %. Catalyst Pt—Cr-L contained platinum loading of 2 wt % and chromium loading of 3 wt %.

Cr was added in acidic solutions by sequential IWI. Pt—Cr-M contains a target loading of 2 wt % Pt and 3 wt % Cr and was synthesized using sequential IWI. $Cr(NO_3)_3 \cdot 9H_2O$, and citric acid were dissolved in Millipore water in a 1:1 molar ratio to yield a blue solution with a pH of 2. The solution was added dropwise to the silica. The obtained Cr precursor was dried at 125° C. for 16 h and then calcined at 350° C. for 3 h and a color change from blue to orange was observed. A second solution was made by dissolving $Pt(NH_3)_4(NO_3)_2$, in Millipore water and adjusting the pH to 11 using 30% ammonium hydroxide solution to yield a colorless solution. The solution was added dropwise to the Cr precursor. The resulting Pt—Cr/$SiO_2$ catalyst was dried at 125° C. for 10-12 h and then calcined at 250° C. for 3 h. The catalyst was reduced in 5% $H_2/N_2$ using a program that ramped from 200° C. for 30 minutes to 250° C. for 30 minutes to 550° C. for 30 minutes.

Cr was added by IWI and then Pt was added by SEA. Pt—Cr-N contains a target loading of 1 wt % Pt and 1 wt % Cr. The Cr precursor was prepared by the IWI technique described above using $Cr(NO_3)_3 \cdot 9H_2O$ and citric acid. After impregnation, the catalyst precursor was dried in an oven at 125° C. for 10-12 h and then calcined at 350° C. for 3 h. 1 wt % Pt was added using the strong electrostatic adsorption (SEA). A Pt solution was made by dissolving $Pt(NH_3)_4(NO_3)_2$ in Millipore water and adjusting the pH to 11 using 30% ammonium hydroxide solution. This was added in a beaker containing 100 mL of Millipore water. The Cr catalyst precursor was added to the beaker and the mixture was stirred for 10 minutes. The solid was recovered using vacuum distillation and was washed three times with Millipore water. The resulting Pt—Cr/$SiO_2$ catalyst was dried at 125° C. for 10-12 h and then calcined at 200° C. for 3 h. The catalyst was reduced in 5% $H_2/N_2$ using a program that ramped from 200° C. for 30 minutes to 250° C. for 30 minutes to 550° C. for 30 minutes.

A series of Pt—Cr (AB-AG) catalysts supported on silica were made with target loading of 2 wt % Pt and 3 wt % Cr and calcined at different temperatures to achieve varying particle sizes. Synthesis followed the sequential IWI technique described above for Pt—Cr (G-K). After the Pt solution was added to the Cr precursor, the resulting catalyst was divided into parts and each was calcined at varying temperatures throughout the range 150° C.-550° C. All catalysts were reduced in 5% $H_2/N_2$ using a program that ramped from 200° C. for 30 minutes to 250° C. for 30 minutes to 550° C. for 30 minutes.

Bimetallic Pt—Ti Catalysts

Bimetallic Pt—Ti (T-U) catalysts were synthesized by incipient wetness impregnation (IWO under controlled pH conditions. For Pt—Ti-T catalyst, 0.405 g of tetraammine platinum nitrate $Pt(NH_3)_4(NO_3)_2$ (Sigma-Aldrich) was dissolved in 3 mL of $H_2O$. A 30% ammonium hydroxide solution (Sigma-Aldrich) was added to the solution until the pH reached 11 before they were added dropwise to 10 g of the support p25 $TiO_2$ (Degussa). This catalyst was dried overnight (for approximately 16 hours) at 125° C., calcined at 225° C. for 3 hours and then reduced at 550° C. in 5% $H_2/N_2$ at 100 $cm^3$/min for 0.5 hours. The Pt—Ti-U catalyst was synthesized in the same manner except that microrutile $TiO_2$ was used as the support. Catalyst Pt—Ti-T contained platinum loading of 2.0 wt % and titanium loading of 59 wt %. Catalyst Pt—Ti-U contained platinum loading of 2.0 wt % and titanium loading of 59 wt %. For the Pt—Ti catalysts, the oxide support is titanium oxide, and a small fraction of the Ti is reduced to form a PtTi bimetallic catalyst.

Catalyst Testing

Propane Dehydrogenation

Propane dehydrogenation kinetics measurements were carried out in a quartz fixed-bed reactor with ⅜-inch ID. The weight of the catalyst used ranged from 0.02 g to 0.20 g. A thermocouple within a stainless-steel thermocouple well was placed at the bottom center of the catalyst bed to measure the reaction temperature inside the bed. The products were analyzed with an Agilent gas chromatograph system equipped with a Flame Ionization Detector (FID). Before each test, the catalyst was first reduced under flowing stream of 5% $H_2$ in $N_2$ while the temperature was raised to 550° C. and held at 550° C. for 30 minutes. For all Pt—Mn and Pt—Ti catalysts, a reaction atmosphere of 2% propane, 1% hydrogen balanced in nitrogen, at 1.0 atm pressure, with a total flow rate of 250 $cm^3$/min was used. Catalyst selectivity was compared at 20% conversion at 550° C. For Pt—V and Pt—Cr catalysts a total flow rate of 200 $cm^3$/min was used in all tests with a propane concentration of 2.5% and a hydrogen concentration of 2.5%.

The propane dehydrogenation performance of Pt, Pt—Mn, Pt—V, Pt—Cr and Pt—Ti catalysts at 550° C. was evaluated using a fixed bed reactor. At this temperature, side reaction propane hydrogenolysis and minor thermal cracking occurred, which produced methane, ethane and ethylene. The initial product selectivity of different catalysts was compared at approximately 20% propane conversion.

Figure 1B:
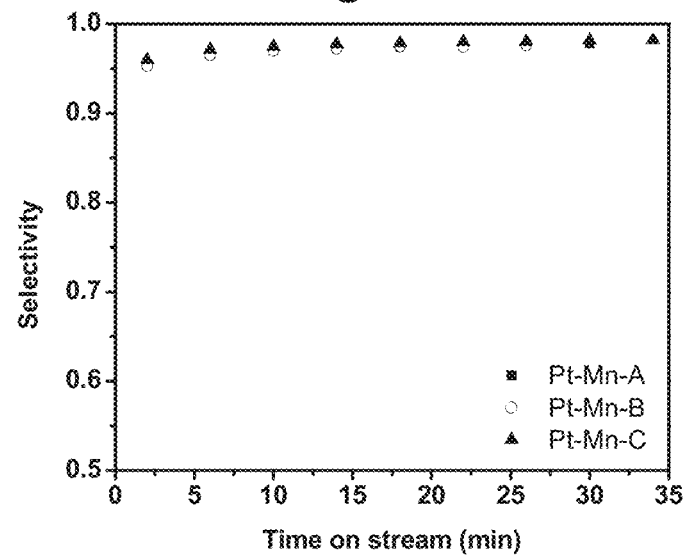

The results for the Pt and Pt—Mn catalysts are shown in Table 1 and FIG. 1. While the Pt catalyst had an initial propylene selectivity of 61% typical of monometallic Pt nanoparticles, the Pt—Mn catalysts of similar particle size showed much higher selectivity, above 95%. Catalysts Pt—Mn-A, B and C started with a selectivity of around 96% and Pt—Mn-D was 99% selective. As the catalyst deactivated with time on stream due to side reaction and coking, selectivity increased with time on stream. After 0.5 hours, while the comparative Pt catalyst quickly deactivated to approximately 10% conversion and reached a selectivity of approximately 80%, both Pt—Mn catalysts showed slower deactivation and were measured with approximately 15% conversion and close to 100% selectivity. The propane dehydrogenation performance of the Pt—Mn-D catalyst was also measured after about 1 day on stream. The conversion at 1 day (11%) did not change much after deactivation in the first hour on stream (14%) and the selectivity was maintained at 100%.

TABLE 1

Catalytic performance of propane dehydrogenation for Pt—Mn catalysts

| Sample | Initial Conversion (%) | Initial Selectivity (%) | Selectivity at 1 h (%) |
|---|---|---|---|
| Pt | 20 | 61 | 80 |
| Pt—Mn-A | 22 | 96 | 100 |

TABLE 1-continued

Catalytic performance of propane dehydrogenation for Pt—Mn catalysts

| Sample | Initial Conversion (%) | Initial Selectivity (%) | Selectivity at 1 h (%) |
|---|---|---|---|
| Pt—Mn-B | 24 | 96 | 100 |
| Pt—Mn-C | 20 | 96 | 100 |
| Pt—Mn-D | 21 | 99 | 100 |

FIG. 1 and Table 2 illustrate the conversion and selectivity of Pt—Mn catalysts A, B, and C in propane dehydrogenation over a 35 minute period. Conversion during propane dehydrogenation was measured in a flow rate of 250 cm$^3$/min of 2% $C_3H_8$, 1% $H_2$ balanced in $N_2$ at 1.0 atm and 550° C. Propane conversion ranged from 15 to 25% and selectivity to the desired propylene product remained greater than 95% throughout this period. The X axis indicates time in minutes and the Y axis indicates mole % propane conversion and selectivity to propylene.

TABLE 2

Performance testing data of PtMn catalysts in FIG. 1

| | Pt—Mn-A | | Pt—Mn-B | | Pt—Mn-C | |
|---|---|---|---|---|---|---|
| time | Initial Conversion (%) | Initial Selectivity (%) | Initial Conversion (%) | Initial Selectivity (%) | Initial Conversion (%) | Initial Selectivity (%) |
| 2 | 21.85 | 95.65 | 22.14 | 95.27 | 19.31 | 96.00 |
| 6 | 19.11 | 96.76 | 19.20 | 96.51 | 17.67 | 97.14 |
| 10 | 17.96 | 97.03 | 17.63 | 96.99 | 17.02 | 97.50 |
| 14 | 16.75 | 97.36 | 16.58 | 97.22 | 16.38 | 97.79 |
| 18 | 16.09 | 97.42 | 15.74 | 97.45 | 16.09 | 97.88 |
| 22 | 15.67 | 97.57 | 15.38 | 97.41 | 15.85 | 98.03 |
| 26 | 15.18 | 97.71 | 14.60 | 97.60 | 15.56 | 98.08 |

Figure 2:
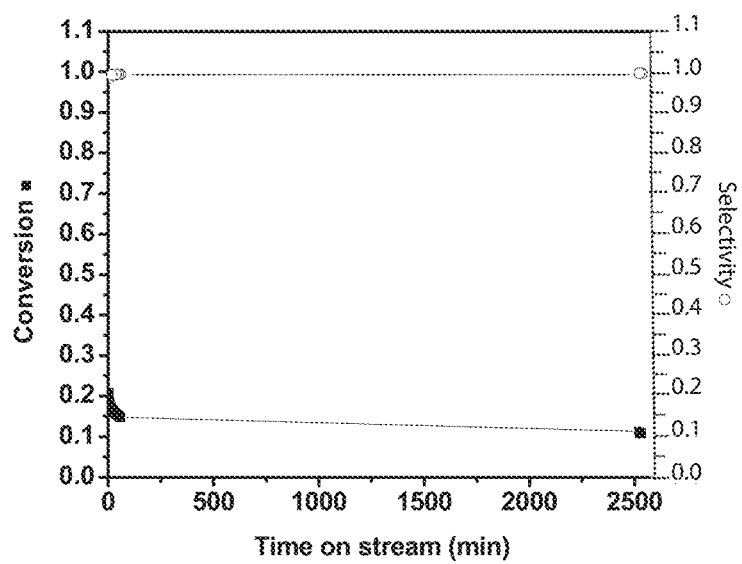
FIG. 2 is a graph of the conversion and selectivity of Pt—Mn catalyst D in propane dehydrogenation.

FIG. 2 illustrates the conversion and selectivity of Pt—Mn catalyst D in propane dehydrogenation over a 42 hour period. Conversion and selectivity was measured in a flow rate of 250 cm$^3$/min of 2% $C_3H_8$, 1% $H_2$ balanced in $N_2$ at 1.0 atm. and 550° C. for 1 day. Propane conversion ranged from 10 to 21% and selectivity to the desired propylene product remained greater than 99% throughout this period. The X axis indicates time in minutes and the Y axis indicates mole % propane conversion and selectivity to propylene.

Propane dehydrogenation test results for Pt—V catalyst are shown in Table 3. For catalyst Pt—V-E, the initial conversion was 18%, after 90 minutes on stream the conversion dropped to 12% and the selectivity improved to 97%. Catalyst F had an initial conversion of 28% at 83% selectivity. After 90 minutes on stream the conversion dropped to 16% and the selectivity rose to 92%. Both catalysts deactivated more slowly than the comparative Pt catalyst, and the extent of deactivation at 90 minutes was lower: 33% for catalyst Pt—V-E and 42% for catalyst Pt—V-F, compared to more than 50% for the comparative Pt catalyst.

Figure 3A:
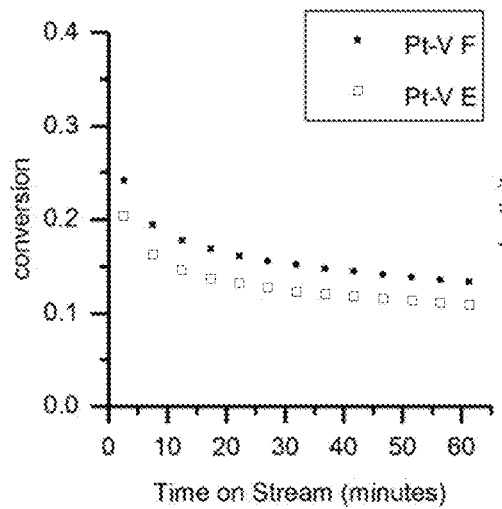
FIG. 3 is a graph of propylene selectivity and propane conversion verses time on stream for Pt—V-F and Pt—V-E at 550° C. with 2.5% propane, 2.5% H2, balance $N_2$.
Figure 3B:
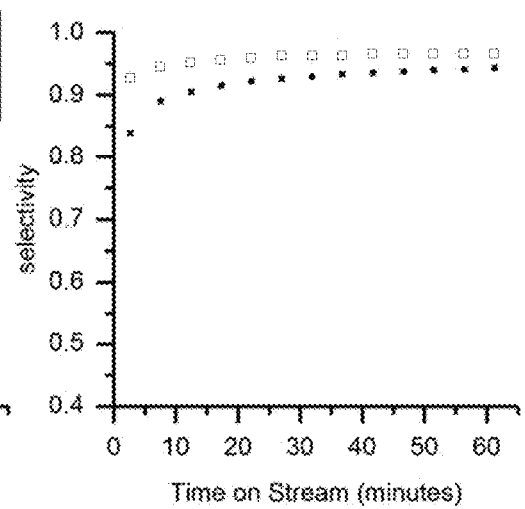

FIG. 3 shows the propylene selectivity and propane conversion of both Pt—V catalysts. Tests were conducted at 550° C., at 1.0 atm, using a total flow rate of 200 ccm. The gas composition was 2.5% propane, 2.5% hydrogen balanced with nitrogen. Both catalysts show some deactivation with time on stream. The Pt—V-E catalyst has a higher initial selectivity than Pt—V F. Both catalysts have a higher selectivity compared to monometallic Pt at equivalent conversion.

TABLE 3

Catalytic performance of propane dehydrogenation for Pt—V catalysts.

| Sample | Initial Conversion (%) | Initial Selectivity (%) | Selectivity at 1 h (%) |
|---|---|---|---|
| Pt—V-E | 18 | 95 | 97 |
| Pt—V-F | 28 | 83 | 92 |

Table 4 lists the selectivity and conversion of Pt—Cr catalysts for propane dehydrogenation at 550° C., at 1.0 atm. Catalysts were tested using a total flow rate of 200 cm$^3$/min with a propane concentration of 2.5% and a hydrogen concentration of 2.5%. After one hour on stream, all three catalysts deactivated by 33% while monometallic platinum catalyst deactivated by more than 50%.

TABLE 4

Catalytic performance of propane dehydrogenation for Pt—Cr catalysts

| Sample | Initial Conversion (%) | Initial Selectivity (%) | Selectivity at 1 h (%) |
|---|---|---|---|
| Pt—Cr-G | 32 | 84 | 95 |
| Pt—Cr-H | 31 | 91 | 97 |
| Pt—Cr-I | 26 | 96 | 99 |
| Pt—Cr-J | 24 | 98 | 99 |
| Pt—Cr-K | 15 | 97 | 99 |
| Pt—Cr-L | 38 | 84 | 94 |

Figure 4A:
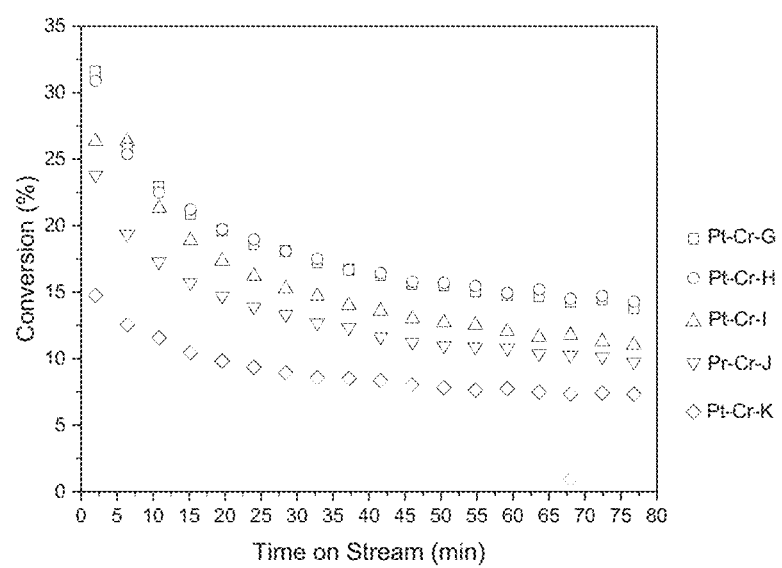
FIG. 4 is a plot of a) Conversion vs time on stream of propane dehydrogenation for Pt—Cr-G through K catalysts and b) Selectivity vs time on stream for Pt—Cr-G through K catalysts.
Figure 4B:
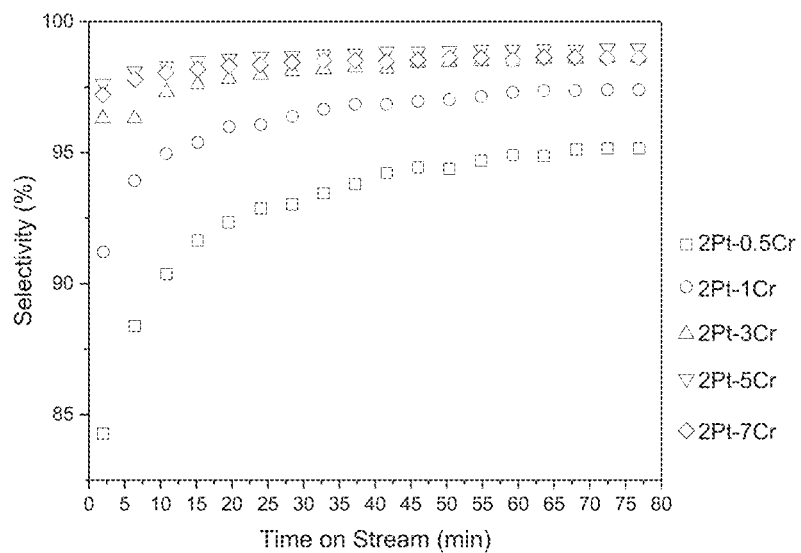

FIG. 4 illustrates the conversion, FIG. 4a, and selectivity, FIG. 4b, of Pt—Cr catalysts G through K in propane dehydrogenation over an hour period. Conversion and selectivity was measured in a flow rate of 200 cm$^3$/min of 2.5% $C_3H_8$, 2.5% $H_2$ balanced in $N_2$ at 1.0 atm and 550° C. Propane conversion ranged from 15 to 32% and selectivity to the desired propylene product stabilized at a value higher than 90% in each instance. The X axis indicates time in minutes and the Y axis indicates mole % propane conversion and selectivity to propylene.

Figure 5:
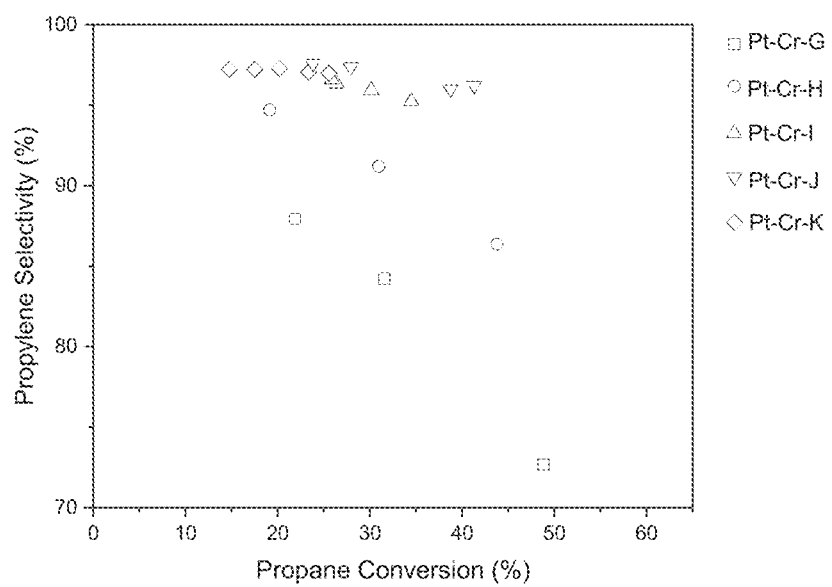
FIG. 5 is a plot of conversion vs. selectivity for Pt—Cr-G through K catalysts.

FIG. 5 illustrates the selectivity at zero deactivation as a function of conversion. As more Cr is used to promote Pt, the slope of these trends approaches zero, indicating a more stable catalyst and suggesting a changing surface composition as Cr loading increases.

Additional catalyst tests of Pt—Cr and comparison Pt only with names Pt-A are given in Table 5.

TABLE 5

Catalytic performance of Pt—Cr, and Pt catalysts for propane dehydrogenation (100 ccm 5% $H_2$ and 100 ccm 5% $C_3H_8$, all at 1.0 atm)

| Sample | Comp | Reactor T (°C) | Initial Selectivity (%) | Selectivity after 1 h (%) | Initial Conversion (%) | Conversion after 1 h (%) |
|---|---|---|---|---|---|---|
| Pt—Cr-G | 2% Pt 0.5% Cr/SiO$_2$ | 550 | 86 | 92 | 33 | 23 |
| Pt—Cr-G | 2% Pt 0.5% Cr/SiO$_2$ | 552 | 88 | 96 | 22 | 11 |
| Pt—Cr-G | 2% Pt 0.5% Cr/SiO$_2$ | 553 | 84 | 95 | 32 | 15 |
| Pt—Cr-G | 2% Pt 0.5% Cr/SiO$_2$ | 549 | 73 | 92 | 49 | 25 |
| Pt—Cr-H | 2% Pt 1% Cr/SiO$_2$ | 548 | 98 | 99 | 5 | 2 |
| Pt—Cr-H | 2% Pt1% Cr/SiO$_2$ | 550 | 93 | 97 | 38 | 25 |
| Pt—Cr-H | 2% Pt 1% Cr/SiO$_2$ | 553 | 97 | 99 | 10 | 2 |
| Pt—Cr-H | 2% Pt 1% Cr/SiO$_2$ | 551 | 86 | 96 | 44 | 23 |
| Pt—Cr-H | 2% Pt 1% Cr/SiO$_2$ | 550 | 91 | 97 | 31 | 15 |
| Pt—Cr-H | 2% Pt 1% Cr/SiO$_2$ | 550 | 95 | 98 | 19 | 9 |
| Pt—Cr-H | 2% Pt 1% Cr/SiO$_2$ | 553 | 93 | 97 | 30 | 17 |
| Pt—Cr-I | 2% Pt 3% Cr/SiO$_2$ | 548 | 99 | 98 | 6 | 6 |
| Pt—Cr-I | 2% Pt 3% Cr/SiO$_2$ | 548 | 98 | 99 | 23 | 16 |
| Pt—Cr-I | 2% Pt 3% Cr/SiO$_2$ | 548 | 98 | 98 | 12 | 7 |
| Pt—Cr-I | 2% Pt3% Cr/SiO$_2$ | 550 | 99 | 99 | 8 | 5 |
| Pt—Cr-I | 2% Pt3% Cr/SiO$_2$ | 550 | 97 | 98 | 24 | 17 |
| Pt—Cr-I | 2% Pt 3% Cr/SiO$_2$ | 550 | 99 | 98 | 5 | 4 |
| Pt—Cr-I | 2% Pt 3% Cr/SiO$_2$ | 550 | 96 | 99 | 26 | 12 |
| Pt—Cr-I | 2% Pt 3% Cr/SiO$_2$ | 550 | 97 | 98 | 6 | 2 |
| Pt—Cr-I | 2% Pt 3% Cr/SiO$_2$ | 552 | 98 | 98 | 11 | 5 |
| Pt—Cr-I | 2% Pt 3% Cr/SiO$_2$ | 553 | 97 | 98 | 26 | 13 |
| Pt—Cr-I | 2% Pt 3% Cr/SiO$_2$ | 551 | 96 | 98 | 30 | 15 |
| Pt—Cr-I | 2% Pt 3% Cr/SiO$_2$ | 553 | 95 | 98 | 34 | 19 |
| Pt—Cr-J | 2% Pt5% Cr/SiO$_2$ | 550 | 98 | 98 | 10 | 7 |
| Pt—Cr-J | 2% Pt5% Cr/SiO$_2$ | 550 | 98 | 99 | 25 | 17 |
| Pt—Cr-J | 2% Pt 5% Cr/SiO$_2$ | 549 | 98 | 98 | 8 | 3 |
| Pt—Cr-J | 2% Pt 5% Cr/SiO$_2$ | 548 | 98 | 99 | 24 | 10 |
| Pt—Cr-J | 2% Pt 5% Cr/SiO$_2$ | 549 | 97 | 98 | 15 | 5 |
| Pt—Cr-J | 2% Pt 5% Cr/SiO$_2$ | 555 | 97 | 99 | 28 | 14 |
| Pt—Cr-J | 2% Pt 5% Cr/SiO$_2$ | 550 | 96 | 98 | 34 | 15 |
| Pt—Cr-J | 2% Pt 5% Cr/SiO$_2$ | 549 | 96 | 98 | 39 | 20 |
| Pt—Cr-K | 2% Pt 7% Cr/SiO$_2$ | 550 | 98 | 98 | 11 | 8 |
| Pt—Cr-K | 2% Pt 7% Cr/SiO$_2$ | 552 | 98 | 98 | 8 | 5 |
| Pt—Cr-K | 2% Pt 7% Cr/SiO$_2$ | 550 | 97 | 99 | 15 | 7 |
| Pt—Cr-K | 2% Pt 7% Cr/SiO$_2$ | 553 | 97 | 98 | 14 | 10 |
| Pt—Cr-K | 2% Pt 7% Cr/SiO$_2$ | 550 | 97 | 98 | 20 | 10 |

TABLE 5-continued

Catalytic performance of Pt—Cr, and Pt catalysts for propane dehydrogenation (100 ccm 5% H₂ and 100 ccm 5% C₃H₈, all at 1.0 atm)

| Sample | Comp | Reactor T (C) | Initial Selectivity (%) | Selectivity after 1 h (%) | Initial Conversion (%) | Conversion after 1 h (%) |
|---|---|---|---|---|---|---|
| Pt—Cr-K | 2% Pt 7% Cr/SiO₂ | 551 | 97 | 98 | 23 | 12 |
| Pt—Cr-K | 2% Pt 7% Cr/SiO₂ | 551 | 97 | 98 | 26 | 13 |
| Pt—Cr-L | 2% Pt 3% Cr/Al₂O₃ | 552 | 84 | 94 | 38 | 19 |
| Pt—Cr-M | 2% Pt 1% Cr/SiO₂ | 551 | 87 | 96 | 30 | 16 |
| Pt—Cr-N | 1% Pt 1% Cr/SiO₂ | 550 | 65 | 89 | 48 | 23 |
| Pt—Cr-O | 2% Pt 3% Cr/SiO₂ | 548 | 97 | 98 | 23 | 13 |
| Pt—Cr-O | 2% Pt 3% Cr/SiO₂ | 550 | 98 | 99 | 9 | 3 |
| Pt—Cr-O | 2% Pt 3% Cr/SiO₂ | 551 | 96 | 99 | 30 | 14 |
| Pt—Cr-P | 2% Pt 3% Cr/SiO₂ | 553 | 98 | 98 | 7 | 5 |
| Pt—Cr-P | 2% Pt 3% Cr/SiO₂ | 554 | 97 | 98 | 20 | 13 |
| Pt—Cr-P | 2% Pt 3% Cr/SiO₂ | 550 | 97 | 98 | 6 | 2 |
| Pt—Cr-P | 2% Pt 3% Cr/SiO₂ | 552 | 96 | 99 | 26 | 12 |
| Pt—Cr-Q | 2% Pt 3% Cr/SiO₂ | 550 | 99 | 98 | 7 | 5 |
| Pt—Cr-Q | 2% Pt 3% Cr/SiO₂ | 547 | 98 | 98 | 6 | 2 |
| Pt—Cr-Q | 2% Pt 3% Cr/SiO₂ | 547 | 96 | 98 | 24 | 11 |
| Pt—Cr-R | 2% Pt 3% Cr/SiO₂ | 545 | 98 | 98 | 5 | 4 |
| Pt—Cr-R | 2% Pt 3% Cr/SiO₂ | 553 | 98 | 98 | 5 | 2 |
| Pt—Cr-R | 2% Pt 3% Cr/SiO₂ | 551 | 97 | / | 13 | / |
| Pt—Cr-S | 2% Pt 3% Cr/SiO₂ | 555 | 98 | 98 | 3 | 3 |
| Pt—Cr-S | 2% Pt 3% Cr/SiO₂ | 550 | 97 | 98 | 6 | 4 |
| Pt-A | 2% Pt/SiO₂ | 550 | 90 | 99 | 17 | 3 |
| Pt-A | 2% Pt/SiO₂ | 552 | 50 | 82 | 41 | 20 |
| Pt-A | 2% Pt/SiO₂ | 548 | 91 | 99 | 18 | 3 |
| Pt-A | 2% Pt/SiO₂ | 549 | 33 | 77 | 60 | 33 |
| Pt-A | 2% Pt/SiO₂ | 549 | 47 | 79 | 52 | 28 |
| Pt-A | 2% Pt/SiO₂ | 551 | 64 | 84 | 28 | 13 |

The results for the Pt—Ti catalysts are shown in Table 6 and FIG. 6. The Pt—Ti catalysts showed high selectivity comparable to that of the other bimetallic catalysts. Both catalysts started with a selectivity of around 96%. As the catalysts deactivated with time on stream due to coking, the selectivity was seen to increase.

TABLE 6

Catalytic performance of propane dehydrogenation for Pt—Ti catalysts

| Sample | Initial Conversion (%) | Initial Selectivity (%) | Selectivity at 1 h (%) |
|---|---|---|---|
| Pt—Ti-T | 19 | 96 | / |
| Pt—Ti-U | 11 | 96 | 99 |

Figure 6A:
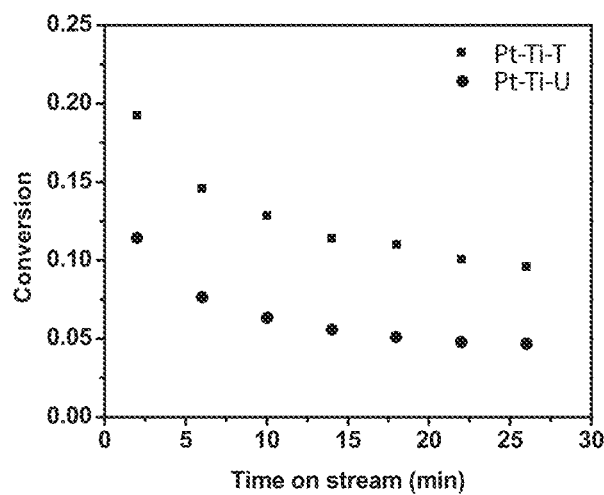
FIG. 6 is a graph of the conversion and selectivity of Pt—Ti catalysts T and U in propane dehydrogenation.
Figure 6B:
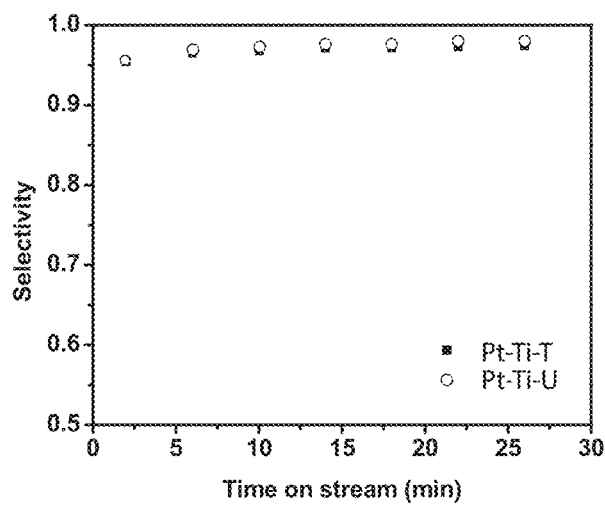

FIG. 6 illustrates the conversion, FIG. 6a, and selectivity, FIG. 6b, of Pt—Ti catalysts T and U in propane dehydrogenation over a 30 minute period. Conversion was measured in a flow rate of 250 cm³/min of 2% C₃H₈, 1% H₂ balanced in N₂ at 1.0 atm and 550° C. Propane conversion ranged from 5 to 19% and selectivity to the desired propylene product remained greater than 96% throughout this period. The X axis indicates time in minutes and the Y axis indicates mole % propane conversion and selectivity to propylene.

Ethane Dehydrogenation

Ethane dehydrogenation kinetics measurements were carried out in the same quartz fixed-bed reactor with ⅜-inch ID. Catalysts Pt—Mn-B and Pt—V-E were tested for ethane dehydrogenation. The ethane dehydrogenation was performed at 750° C., with a total flow rate of 120 cm³/min, with an ethane concentration of 25% with balance nitrogen, at 1.0 atm pressure. At 750° C., the equilibrium conversion of ethane to ethylene is 75%. Initial conversions for the catalyst were 42 and 39 percent for Pt—Mn-B and Pt—V-E respectively. The catalysts showed little deactivation and maintained high selectivity to ethylene of greater than 90% over the course of the one-day test.

Figure 7:
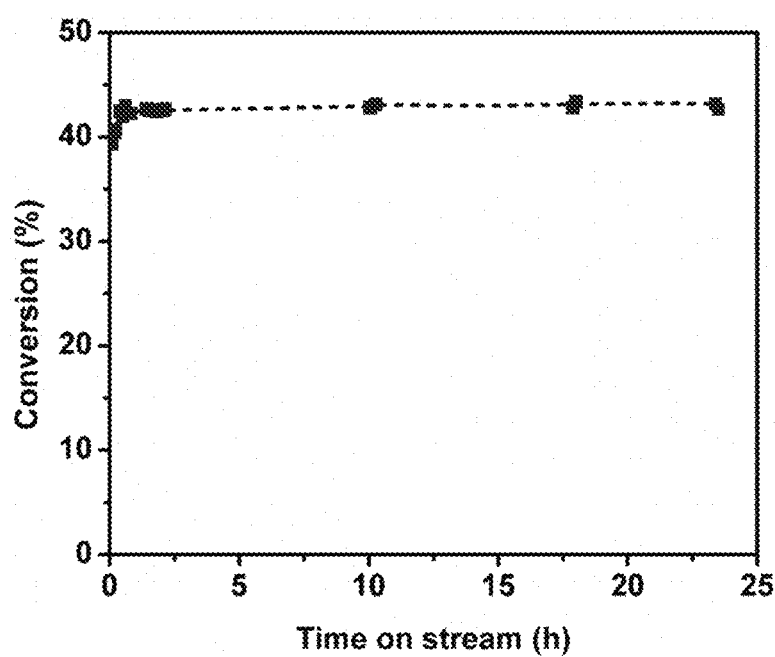
FIG. 7 is a graph of the conversion vs time of the Pt—Mn catalyst B in ethane dehydrogenation at 750 C with 25% ethane balance N2.

Ethane dehydrogenation test results are shown in Table 7 and FIG. 7 for Pt—Mn-B.

TABLE 7

Catalytic performance for ethane dehydrogenation for Pt—Mn-B and Pt—V-E catalysts.

| Sample | Initial Conversion (%) | Initial Selectivity (%) | Conversion at 18 h (%) | Selectivity at 18 h (%) |
|---|---|---|---|---|
| Pt—Mn-B | 42 | 97 | 43 | 92 |
| Pt—V-E | 39 | 97 | 42 | 92 |

FIG. 7 illustrates the conversion vs time on stream of Pt—Mn catalyst B in ethane dehydrogenation for 1 day. Conversion of ethane was measured in a flow rate of 120 cm$^3$/min of 25% $C_2H_6$ balanced in $N_2$ at 1.0 atm and 750° C. Ethane conversions ranged from 39 to 43 percent and selectivity to the desired ethylene product remained greater than 92% throughout this period.

Figure 8A:
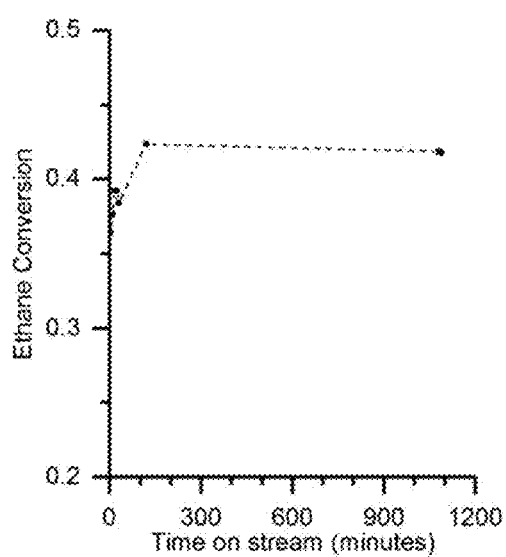
FIG. 8 is a graph of ethane conversion and ethylene selectivity vs. time on stream for Pt—V E at 730° C. with 25% ethane balance $N_2$.
Figure 8B:
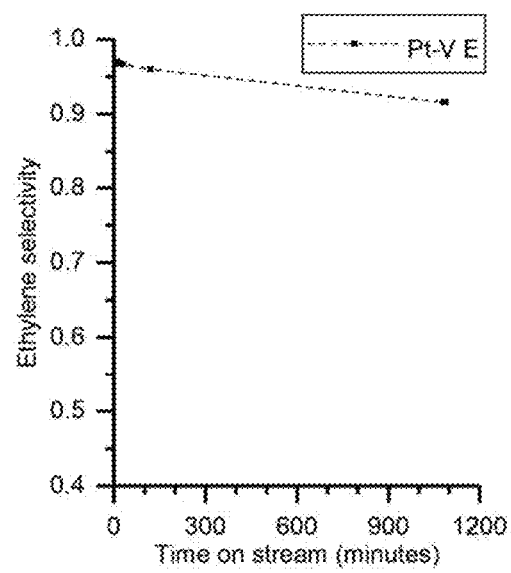

FIG. 8 shows the ethylene selectivity and ethane conversion for Pt—V-E at 730° C. with an ethane concentration of 25%. Initially, conversion is close to 35%, but after an hour on stream the conversion increases to 42% and is stable at that value over the next 24 hours. Initially selectivity is 97%, after 24 hours on stream, the selectivity drops to 92%.

Catalyst Structure Analysis

EXAFS analysis of catalysts was performed at the BM 10 line at the advanced photon source, Argonne National Laboratory. Samples for EXAFS were ground into a fine powder and pressed into a cylindrical hole of a sample holder for analysis. Before analysis the samples were reduced at 550° C. in flowing hydrogen (3% $H_2$/He) for 30 minutes. After reduction, the samples were purged in helium at high temperature and then cooled to room temperature in helium. The helium was purified by a Matheson PUR-gas triple purifier cartridge with a copper trap. EXAFS data analysis was performed using WINXAS 3.1 software using a least squares fit of both R and K space data. Results from the analysis are shown in Table 8.

TABLE 8

EXAFS results for Pt—Mn, Pt—V, Pt—Cr and Pt—Ti catalysts

| Sample | Scattering Pair | Coordination number | Bond distance (Å) | $\Delta\sigma^2$ | $E_0$ |
|---|---|---|---|---|---|
| Pt | Pt—Pt | 8.7 | 2.75 | .003 | −0.4 |
| Pt—Mn-A | Pt—Pt | 6.8 | 2.73 | .004 | −2.6 |
|  | Pt—Mn | 1.3 | 2.72 | .004 | 3.9 |
| Pt—Mn-D | Pt—Pt | 6.3 | 2.72 | .004 | −2.9 |
|  | Pt—Mn | 1.9 | 2.72 | .004 | 3.4 |
| Pt—V-E | Pt—Pt | 7.1 | 2.74 | .003 | −1.2 |
|  | Pt—V | 1.7 | 2.66 | .003 | 2.8 |
| Pt—V-F | Pt—Pt | 7.9 | 2.74 | .003 | −1.7 |
|  | Pt—V | 1.5 | 2.66 | .003 | 2.8 |
| Pt—Cr-G | Pt—Pt | 7.7 | 2.74 | .003 | −1.5 |
|  | Pt—Cr | 1.0 | 2.67 | .005 | −2.5 |
| Pt—Cr-K | Pt—Pt | 8.7 | 2.75 | .003 | −0.5 |
|  | Pt—Cr | 1.2 | 2.67 | .005 | −2.9 |
| Pt—Ti-T | Pt—Pt | 6.0 | 2.73 | .004 | 3.6 |
|  | Pt—Ti | 0.9 | 2.63 | .004 | 3.6 |
| Pt—Ti-U | Pt—Pt | 5.2 | 2.70 | .008 | 0.8 |
|  | Pt—Ti | 1.4 | 2.62 | .010 | 0.8 |

XRD analysis was performed at the ID11 beamline of the advanced photon source, Argonne national laboratory. Samples were measured in the transmission Laue mode with a wide area detector. Phases identified are listed in Table 9. Catalyst Pt—Mn-A, both of the Pt—V and the Pt—Cr catalysts have a core shell structure, with an alloy shell and a Pt core, while Pt—Mn-D was fully alloyed.

TABLE 10

Crystal structure of Pt, Pt—Mn, Pt—V and Pt—Cr catalysts from XRD pattern analysis

| Sample Name | Crystal Phase |
|---|---|
| Pt | Pt (FCC) |
| Pt—Mn-A | Pt + $Pt_3$Mn |
| Pt—Mn-D | $Pt_3$Mn ($Cu_3$Au structure type) |
| Pt—V-E | Pt + $Pt_3$V ($Cu_3$Au structure type) |
| Pt—V-F | Pt + $Pt_3$V ($Cu_3$Au structure type) |
| Pt—Cr-G | Pt + $Pt_3$Cr |
| Pt—Cr-K | Pt + $Pt_3$Cr + $Cr_2O_3$ |

An embodiment of the present disclosure is a bimetallic catalyst composition that includes a Group VIII noble metal, a metal selected from the group consisting of manganese, vanadium, chromium, titanium, and combinations thereof, and a support material. The Group VIII noble metal can be selected from the group consisting of platinum, palladium, osmium, ruthenium, iridium, rhodium, and combinations thereof. The Group VIII noble metal can be present in an amount ranging from 0.001 wt % to 40 wt % on an elemental basis of the catalyst composition. The manganese, vanadium, chromium, titanium, and combinations thereof, can be present in an amount from 0.001 wt % to 10 wt % on an elemental basis of the catalyst composition and are present, at least partially in the metallic phase.

The manganese, vanadium, chromium, titanium, and combinations thereof can, at least partially be present in an alloy state. The support material can be selected from the group of silica, silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof.

An alternate embodiment of the disclosure is a process for the dehydrogenation of alkanes to olefins that includes providing a bimetallic catalyst comprising a Group VIII noble metal along with a metal selected from the group consisting of manganese, vanadium, chromium, titanium, and combinations thereof on a support. The catalyst is then contacted with a feedstream of light alkanes under dehydrogenation conditions. A dehydrogenation reaction occurs converting a portion of the light alkanes to their corresponding olefins. The Group VIII noble metal can be selected from the group of platinum, palladium, osmium, rhodium, ruthenium, iridium, and combinations thereof and can be present in an amount ranging from 0.001 wt % to 10 wt %. The support can be selected from the group consisting of silica, silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the metals are added using sequential incipient wetness impregnation. In an embodiment the metals are added using a co-impregnation method.

The feedstream can optionally include hydrogen. The feedstream can optionally include an inert gas. The feedstream can optionally include steam. The feedstream can include propane and the reaction can have selectivity to propylene of at least 90%, optionally at least 94%, optionally at least 98%. In an embodiment the conversion of propane to olefins is at least 10%, optionally at least 15%, optionally at least 20%. In an embodiment the conversion of the propane to olefins is at least 10% with selectivity to propylene of at least 90% and the catalytic dehydrogenation reaction continues for at least 30 minutes, optionally at least 1 hour, optionally at least 2 hours, optionally at least 5 hours, optionally at least 10 hours, optionally at least 15 hours, optionally at least 20 hours, optionally at least 30 hours, optionally at least 40 hours, optionally at least 50 hours.

The feedstream can include ethane and the reaction can have selectivity to ethylene of greater than 90%, optionally at least 94%, optionally at least 98%. In an embodiment the conversion of ethane to olefins is at least 10%, optionally at least 20%, optionally at least 30%, optionally at least 40%. In an embodiment the conversion of ethane to olefins is at least 10% with selectivity to ethylene of greater than 90% and the catalytic dehydrogenation reaction continues for at least 30 minutes, optionally at least 1 hour, optionally at least 2 hours.

In an embodiment the feedstream includes $C_2$ to $C_5+$ alkanes and the reaction has selectivity to $C_2$ to $C_5+$ olefins of greater than 90%. Optionally the conversion of $C_2$ to $C_5+$ alkanes to $C_2$ to $C_5+$ olefins is at least 10%. In an embodiment the conversion of $C_2$ to $C_5+$ alkanes to $C_2$ to $C_5+$ olefins is at least 10% with selectivity of $C_2$ to $C_5+$ alkanes to $C_2$ to $C_5+$ olefins is greater than 90% and continues for at least 30 minutes, optionally at least 1 hour, optionally at least 2 hours, optionally at least 5 hours.

A further embodiment is a method of making a dehydrogenation catalyst that includes providing a support material, adding to the support material a first metal selected from the group consisting of manganese, vanadium, chromium, titanium, and combinations thereof to form a first catalyst material, and then adding to the first catalyst material a second metal that is a Group VIII noble metal to make a second catalyst material. The second catalyst material is then calcined and reduced to form a dehydrogenation catalyst.

The Group VIII noble metal can be selected from the group consisting of platinum, palladium, osmium, ruthenium, iridium, rhodium, and combinations thereof. The Group VIII noble metal can be present in an amount ranging from 0.01 wt % to 10 wt % on an elemental basis of the dehydrogenation catalyst composition. The first metal can be present in an amount from 0.01 wt % to 10 wt % on an elemental basis of the dehydrogenation catalyst composition and are present, at least partially in the metallic phase and/or in an alloy state. The support can be selected from the group consisting of silica, silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the support is selected from the group consisting of silicon dioxide, aluminum oxide, titanium dioxide, and metal modified silica. In an embodiment the metals are added using sequential incipient wetness impregnation. In an embodiment the metals are added using a co-impregnation method.

The text above describes one or more specific embodiments of a broader disclosure. The disclosure also can be carried out in a variety of alternate embodiments and thus is not limited to those described here. The foregoing description of an embodiment of the disclosure has been presented for the purposes of illustration and description. It is not intended to be exhaustive or to limit the disclosure to the precise form disclosed. Many modifications and variations are possible in light of the above teaching. It is intended that the scope of the disclosure be limited not by this detailed description, but rather by the claims appended hereto.

What is claimed is:

1. A process for catalytically dehydrogenating alkanes to olefins comprising:
    providing a supported metal alloy catalyst comprising:
        a first metal selected from the group consisting of platinum, palladium, osmium, rhodium, rubidium, iridium, and combinations thereof,
        a second metal selected from the group consisting of manganese, vanadium, chromium, titanium, and combinations thereof, and
        a support to form a supported metal alloy catalyst, wherein at least some of the metals on the support have a zero valent state;
    contacting the supported metal alloy catalyst with a feedstream comprising one or more $C_2$ to $C_{5+}$alkanes; and
    dehydrogenating a portion of the one or more $C_2$ to $C_{5+}$alkanes to one or more $C_2$ to $C_{5+}$olefins in the presence of the supported metal alloy catalyst.

2. The process according to claim 1, wherein the first metal is selected from the group consisting of platinum, palladium, and combinations thereof.

3. The process according to claim 1, wherein the first metal is present in an amount ranging from 0.001 wt % to 40 wt % on an elemental basis of the metal alloy catalyst.

4. The process according to claim 1, wherein the manganese, vanadium, chromium, titanium, and combinations thereof is present in an amount from 0.01 to 40 wt % on an elemental basis of the metal alloy catalyst and present, at least partially in a metallic phase and at least partially in an alloy phase.

5. The process according to claim 1, wherein the support is selected from the group consisting of silicon dioxide, titanium dioxide, aluminum oxide, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof.

6. The process according to claim 1, wherein the support is selected from the group consisting of silicon dioxide, aluminum oxide, titanium dioxide, and metal modified silica.

7. The process according to claim 1, wherein the first metal is selected from the group consisting of platinum, palladium, and combinations thereof and is present in an amount ranging from 0.01 wt % to 10 wt %, wherein the manganese, vanadium, chromium, titanium, and combinations thereof is present in an amount from 0.01 to 10 wt % and wherein the support is selected from the group consisting of silicon dioxide, aluminum oxide, titanium dioxide, and metal modified silica.

8. The process according to claim 1, wherein the supported metal alloy catalyst is calcined and reduced prior to contact with the feedstream.

9. The process according to claim 1, wherein the feedstream is produced from a shale formation.

10. A process for catalytically transforming a natural gas liquid (NGL), comprising:
providing a hydrocarbon containing gas stream comprising one or more light alkanes chosen from the group consisting of $C_2$, $C_3$, $C_4$, $C_5$, and combinations thereof;
catalytically dehydrogenating at least a portion of the light alkanes in the presence of at least one dehydrogenation catalyst to provide one or more corresponding alkene derivatives, wherein the at least one dehydrogenation catalyst comprises:
a first metal selected from the group consisting of platinum, palladium, osmium, rhodium, rubidium, iridium, and combinations thereof,
a second metal selected from the group consisting of manganese, vanadium, chromium, titanium, and combinations thereof, and
a support, wherein at least some of the metals on the support have a zero valent state.

11. The process according to claim 10, wherein the hydrocarbon containing gas stream is produced from a shale formation.

12. The process according to claim 10, wherein the hydrocarbon containing gas stream is derived from a natural gas liquid (NGL).

13. The process according to claim 10, wherein the first metal is selected from the group consisting of platinum, palladium, iridium, and combinations thereof.

14. The process according to claim 10, wherein the support is selected from the group consisting of silicon dioxide, titanium dioxide, aluminum oxide, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof.

15. The process according to claim 10, wherein the support is selected from the group consisting of silicon dioxide, aluminum oxide, titanium dioxide, and metal modified silica.

16. The process according to claim 10, wherein the first metal is selected from the group consisting of platinum, palladium, and combinations thereof and is present in an amount ranging from 0.01 wt % to 10 wt %, wherein the manganese, vanadium, chromium, titanium, and combinations thereof, is present in an amount from 0.01 to 10 wt % and wherein the support is selected from the group consisting of silicon dioxide, aluminum oxide, titanium dioxide, and metal modified silica.

17. A process for catalytically transforming a natural gas liquid (NGL), comprising:
providing a hydrocarbon containing gas stream that is derived from a shale formation, the stream comprising one or more light alkanes chosen from the group consisting of $C_2$, $C_3$, $C_4$, $C_5$, and combinations thereof;
catalytically dehydrogenating at least a portion of the light alkanes in the presence of at least one metal alloy dehydrogenation catalyst to provide one or more corresponding alkene derivatives, wherein the at least one metal alloy dehydrogenation catalyst comprises:
a first metal selected from the group consisting of platinum, palladium, and combinations thereof,
a second metal selected from the group consisting of manganese, vanadium, chromium, titanium, and combinations thereof, and
a support, wherein at least some of the metals on the support have a zero valent state and wherein the metal alloy catalyst is calcined and reduced prior to contact with the light alkanes.

18. The process according to claim 17, wherein the hydrocarbon containing gas stream is derived from a natural gas liquid (NGL).

19. The process according to claim 17, wherein the first metal is present in an amount ranging from 0.01 wt % to 10 wt %, wherein the manganese, vanadium, chromium, titanium, and combinations thereof is present in an amount from 0.01 to 10 wt % and wherein the support is selected from the group consisting of silicon dioxide, aluminum oxide, titanium dioxide, and metal modified silica.

20. The process according to claim 17, wherein the catalyst comprises 0.01 wt % to 10 wt % palladium and 0.01 to 10 wt % chromium or titanium, wherein the support is selected from the group consisting of silicon dioxide, aluminum oxide, titanium dioxide, and metal modified silica.

* * * * *